United States Patent [19]

Hogenkamp

[11] Patent Number: 5,449,795
[45] Date of Patent: Sep. 12, 1995

[54] PROCESS FOR SYNTHESIS OF STEROIDAL ALLYLIC TERT. ALCOHOLS

[75] Inventor: Derk J. Hogenkamp, Long Beach, Calif.

[73] Assignee: CoCensys, Inc., Irvine, Calif.

[21] Appl. No.: 195,719

[22] Filed: Feb. 14, 1994

[51] Int. Cl.$^6$ ............................................. C07J 75/00
[52] U.S. Cl. .................................... 552/530; 552/531; 552/532; 552/533; 552/534; 552/603; 540/95; 540/96; 540/97; 540/108; 540/109; 540/112
[58] Field of Search ............... 552/530, 531, 532, 533, 552/603, 534; 540/95, 96, 97, 108, 109, 112

[56] References Cited

U.S. PATENT DOCUMENTS 3,971,777  7/1976  Rousseau et al. .............. 260/239.5
5,232,917  8/1993  Bolger et al. ................... 514/176

OTHER PUBLICATIONS

Corey and Chaykovsky, "Dimethyloxosulfonium Methylide ((CH$_3$)$_2$SOCH$_2$) and Dimethylsulfonium Methylide ((CH$_3$)$_2$SCH$_2$). Formation and Application to Organic Synthesis", *J. Am. Chem. Soc.* 87 (6):1353–1364 (1965).

Guittet, E. and Julia, S., "A Simple Synthesis of 3,7-dimethylocta-1,5(E),7-trien-3-ol (E-Hotrienol)", *Synth. Comm.* 9 (4):317–323 (1979).

Okamura et al., "1-Arylsulfinyl-1-alken-1-yllithium", *Chem. Lett.*:517–520 (1978).

Sharma et al., "Synthesis of sultines via tert-butyl hydroxyalkyl sulfoxides", *Can. J. Chem.* 54:3012–3025 (1976).

Takano et al., "A Facile Synthesis of (R)-1-Benzyloxy-3-buten-2-ol", *Synthesis* (August):610–611 (1988).

Trost et al., "New Synthetic Reactions. Sulfenylations and Dehydrosufenylations of Esters and Ketones", *J. Am. Chem. Soc.* 98(16):4887–4902 (1976).

Primary Examiner—Johann Richter
Assistant Examiner—Kimberly J. Kestler
Attorney, Agent, or Firm—Sterne, Kessler, Goldstein & Fox

[57] ABSTRACT

A method for the preparation of a steroidal allylic tertiary alcohol is disclosed which involves the deprotonation of a sulfoxide with a strong base which is capable of deprotonating the methine proton which is α to the sulfoxide, in an inert solvent to give the anion; reaction of the anion with a steroidal spiro-2'-oxirane to give a steroidal γ-hydroxysulfoxide; and thermolysis in the presence of a base other than calcium carbonate to give the steroidal allylic tertiary alcohol.

10 Claims, No Drawings

PROCESS FOR SYNTHESIS OF STEROIDAL ALLYLIC TERT. ALCOHOLS

FIELD OF THE INVENTION

The invention is in the field of synthetic organic chemistry. In particular, the invention relates to a method for preparing steroidal allylic tertiary alcohols.

BACKGROUND OF THE INVENTION

There are a number of examples in the literature of the preparation of allylic alcohols from epoxides and methyl sulfoxides. For example, Takano, S.; Tomita, S.; Iwabuchi, Y.; Ogasawara, K. *Synthesis* 610–611 (1988), report the use of sodium dismylate, obtained from dimethylsulfoxide and sodium hydride, to open the epoxide 1 to give the γ-hydroxysulfoxide 2. Heating 2 in refluxing 1,2-dichlorobenzene gives the allylic alcohol 3. (See, Scheme I).

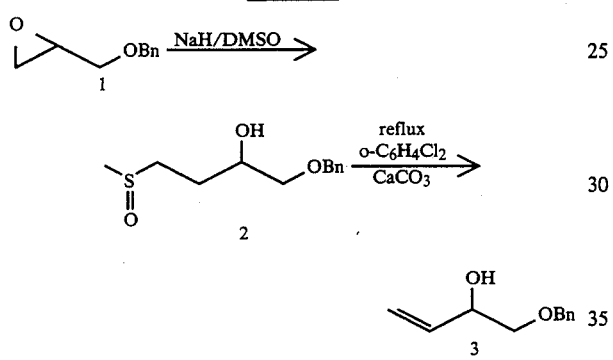

Guittet, E.; Julia, Sylvestre, *J. Synth. Comm.* 9:317–323 (1979), disclose the reaction of the lithium anion of the sulfoxide 4 with epoxide 5. The product (6) is then heated in refluxing toluene to give 3,7-dimethylocta-1,5(E),7-trien-3-ol (7). (See, Scheme II.)

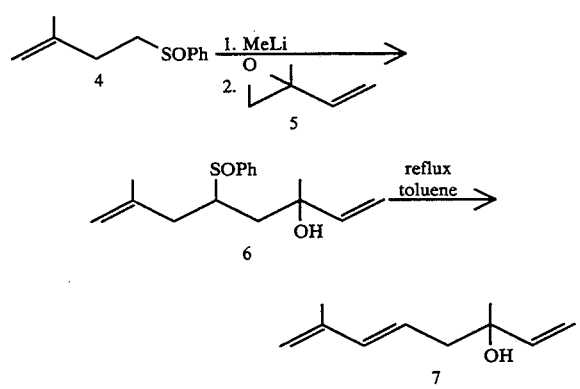

Other references disclose the preparation of γ-hydroxysulfoxides, but do not mention the thermolysis of these compounds to give the corresponding olefin. For example, German patent 2,541,659, Apr. 8, 1976, discloses the opening of epoxide 10 with methyl tert-butyl sulfoxide anion to give sulfoxide 11 which was cyclized to a sulfinate ester 12 (Scheme III).

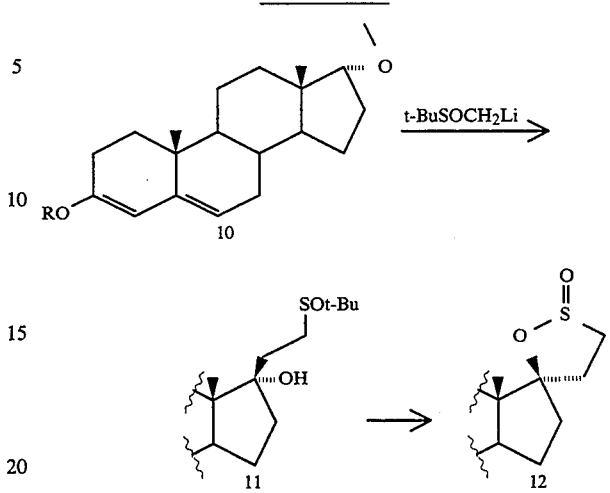

Sharma, N. K.; de Reinach-Hirtzbach, F.; Durst, T., *Can. J. Chem.* 54:3012 (1976) disclose the reaction of methyl tert-butyl sulfoxide anion with propylene oxide and styrene oxide.

Okamura, H. *et al. Chem. Lett.* 517–520 (1978), disclose the reaction of the lithium anion of vinyl aryl sulfoxides with propylene oxide and styrene oxide.

There are a very large number of literature references describing the thermal elimination of sulfoxides to form alkenes. See, for example, Trost, B. M.; Salzmann, T. N.; Hiroi, K. *J. Am. Chem. Soc.* 98:4887 (1976) and the references cited therein.

When attempting to utilize the teachings of the prior art mentioned above, certain difficulties were encountered. For example, (3-R)-20,20-ethylenedioxy-5α-pregnane-spiro-2'-oxirane was treated with sodium dismylate to give 20,20-ethylenedioxy-3β-hydroxy-3β-[2-(methylsulfinyl)ethyl]-5α-pregnane. When this compound was refluxed with calcium carbonate in p-isopropyltoluene (see Takano et al., supra), extensive dehydration of the tertiary alcohol occurred. Adding 2,4,6-collidine to the reaction mixture did not prevent the dehydration.

An object of the present invention is to provide a novel and mild method to generate steroidal allylic tertiary alcohols without dehydration.

SUMMARY OF THE INVENTION

It is an object of this invention to provide a method for preparing steroidal allylic tertiary alcohols that offers significant advantages over the conventional reagents.

In particular, the invention relates to a method for the preparation of a steroidal allylic tertiary alcohol, comprising (a) reaction of a sulfoxide having the formula R—S-(O)CR$_1$R$_2$H, wherein R is an alkyl or more preferably aryl, substituted aryl, heteroaryl or substituted heteroaryl group, R$_1$ is hydrogen, lower alkyl, aryl, substituted aryl or halogen; and R$_2$ is hydrogen or lower alkyl; with a base which is capable of deprotonating the methine hydrogen which is α to the sulfoxide, to give an anion;

(b) reaction of the anion obtained in step (a) with a steroidal spiro-2'-oxirane to give a steroidal γ-hydroxysulfoxide;

(c) thermolysis of the steroidal γ-hydroxysulfoxide obtained in step (b) in the presence of a base other than calcium carbonate to give the steroidal allylic tertiary alcohol.

DETAILED DESCRIPTION OF THE PREFERRED EMBODIMENTS

The invention relates to a process for the synthesis of a steroidal allylic tertiary alcohols by the preparation of a steroidal spiro-2'-oxirane, the ring opening of the steroidal spiro-2'-oxirane with a sulfoxide anion to give the γ-hydroxysulfoxide and the thermolysis of the γ-hydroxysulfoxide in the presence of a base other than calcium carbonate. The steroidal spiro-2'-oxirane may be prepared from a steroidal ketone by reaction with, for example, trimethylsulfoxonium halide/potassium t-butoxide or, when the ketone is unsaturated or a dienone, trimethylsulfonium halide/sodium hydride (Corey and Chaykovsky, J. Amer. Chem. Soc. 87:1353 (1965)). Preferred ketones which may be used to prepare the spiro-2'-oxiranes are in the cyclopentanopolyhydrophenanthrene series, for example, androstanolones such as androsterones; dihydrotestosterones; androstenolones such as dehydroandrosterones, androstanediones, androstenediones; etio-cholenyl-17-aldehyde with the aldehyde protected, for example, as the cyclic ethylene ketal; estrone; hexahydroestrone; equilin; pregnanolones; pregnenolones; pregnanediones; pregnenediones; compounds of the suprarenal cortical hormone series; cholestanone; cholestenone; as well as analogous ketones of the sterol series or derivatives thereof such as ethers (including alkyl dialkylarylsilyl and trialkylsilyl ethers), mono-enol derivatives of diketones and the like.

Examples of allylic tert. alcohols which can be produced according to the invention include compounds having Formulae I and II, wherein $R_1$ can be hydrogen, lower alkyl, aryl, substituted aryl or halogen; $R_2$ can be hydrogen or lower alkyl; $R_3$ can be hydrogen or methyl; $R_4$ and $R_5$ can be oxo or hydrogen or hydroxy, but not both oxo, or both hydrogen or both hydroxy; and $R_6$ can be methyl or methoxy. Both of the compounds having Formulae I and II can have 5α- or 5β configurations. Double bonds can be present at the 1, 4, 5(6), 8(14), 9(11), 11 and 15 positions.

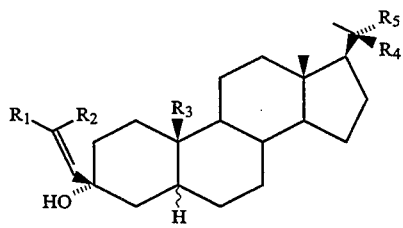

I

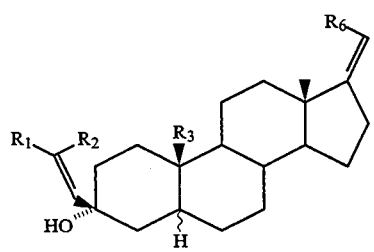

II

Preferably, the alkyl groups are $C_{1-10}$ and the aryl groups are $C_{6-14}$.

Typical $C_{6-14}$ aryl groups include phenyl, naphthyl, phenanthryl, anthracyl, indenyl, azulenyl, biphenyl, biphenylenyl and fluorenyl groups.

Typical heteroaryl groups include pyridyl, 2-benzo[b]thienyl, 2-naphtho[2,3-b]thienyl, thianthrenyl, xanthenyl, phenoxanthinyl, 2H-pyrrolyl, pyrrolyl, imidazolyl, pyrazolyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinazolinyl, cinnolinyl, pteridinyl, 5aH-carbazolyl, carbozolyl, β-carbolinyl, phenanthridinyl, acrindinyl, perimidinyl, phenanthrolinyl, phenazinyl, isothiazolyl, phenothiazinyl, isoxazolyl, furazanyl and phenoxazinyl groups.

Examples of substituents on the aryl and heteroaryl group include dialkylamino, halo, alkyl, alkenyl, alkynyl, aryl, and alkoxy.

Typical substituted aryl groups include any of the $C_{6-14}$ aryl groups substituted by one or more dialkylamino, fluoro, chloro, cyano, alkyl, alkenyl, and alkynyl groups, e.g. 2-chlorophenyl, 2,4-difluorophenyl and the like.

Typical dialkylamino groups include $NR_5R_6$, wherein $R_5$ and $R_6$ are $C_{1-4}$ alkyl groups.

Typical halo groups include fluorine, chlorine, bromine and iodine.

Typical $C_{1-10}$ alkyl groups include methyl, ethyl, propyl, isopropyl, butyl, sec.-butyl, and tert.-butyl groups as well as side chain groups present at the C-17 position of cholestane steroids such as 6-methyl-2-heptyl and 5-ethyl-6-methyl-2-heptyl groups.

Typical $C_{2-10}$ alkenyl groups include vinyl, allyl, 1-butenyl, 2-butenyl, 3-butenyl, isobutenyl and 6-methyl-2-(3-heptenyl) groups.

Typical $C_{2-10}$ alkynyl groups include propargyl, 1-propynyl, 2-propynyl, 1-butynyl, 2-butynyl and 3-butynyl groups.

Typical haloalkyl groups include $C_{1-10}$ alkyl groups substituted by one or more fluorine atoms, e.g., fluoromethyl, difluoromethyl, trifluoromethyl, pentafluoroethyl, 1,1-difluoroethyl and trichloromethyl groups.

Typical alkoxy groups include any one of the $C_{1-10}$ alkyl groups mentioned above linked by oxygen.

Particular examples of compounds which can be made according to the present invention include the 17α-ethenyl compounds Norgesterone and Norvinisterone, entries 6619 and 6637, respectively, in the Merck Index, eleventh edition). When Norgesterone is combined with ethynylestradiol, the preparation is called Vestalin.

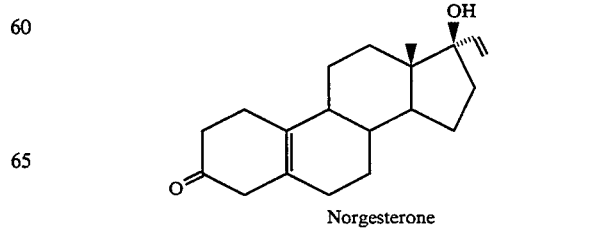

Norgesterone

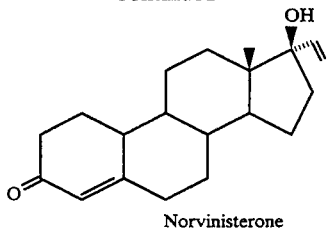
Norvinisterone

Other examples of allylic steroidal tert. alcohols which can be prepared include 3β-ethenyl-3α-hydroxy-5β-pregnan-20-one; 11α-dimethylamino-3β-ethenyl-3α-hydroxy-5β-pregnan-20-one; 11α-dimethylamino-3β-ethenyl-3α-hydroxy-5α-pregnan-20-one; 3β-ethenyl-3α-hydroxy-5β-pregn-11-en-20-one; 3α,17β-dihydroxy-17α-ethenyl-5α-androstane; 3α,17β-dihydroxy-17α-ethenyl-3β-methyl-5α-androstane and 3β-ethenyl-3α-hydroxy-5β-pregn-11-en-20-one.

In particular, this invention relates to a process for the synthesis of 3β-ethenyl-3α-hydroxy-5α-pregnan-20-one (16, see scheme 1 below) from 20,20-ethylenedioxy-3(R)-5α-pregnan-3-spiro-2'-oxirane(14). The first step involves the opening of an epoxide with an anion of methyl phenyl sulfoxide to give the γ-hydroxysulfoxide (15). With heating, 15 undergoes elimination to give 20,20-ethylenedioxy-3β-ethenyl-3α-hydroxy-5α-pregnane and benzenesulfenic acid. Deprotection of the 20-ketal then affords 16. The thermolysis reaction requires the presence of a base to prevent dehydration of 16.

The process of this invention can be performed by reacting two equivalents of a strong base with about two equivalents of the sulfoxide in an inert ether solvent such as THF, at a reaction temperature of about −78° to −10° C. under an inert atmosphere such as dry $N_2$ or argon. Examples of such strong bases include lithium dialkylamides such as lithium diisopropylamide, lithium diethylamide, and the like. The reaction time for this step is normally 5–60 minutes. The generated reagent, which is maintained at −78° to −10° C., is then reacted with about one equivalent of a steroidal spiro-2'-oxirane compound in an inert ether solvent or added as a solid at about −78° to −10° C. Of course, where the spiro-2'-oxirane comprises an acidic proton on a hydroxy group, the group should first be protected (e.g. with t-butyldimethylsilyl chloride) or an excess of the sulfoxide anion should be employed (one equivalent for each acidic proton).

Examples of sulfoxides having formula R—S-(O)CR$_1$R$_2$H which may be used in the practice of the invention include methyl phenyl sulfoxide, ethyl phenyl sulfoxide, methyl 2-pyridyl sulfoxide and the like. Preferably, the sulfoxide is an alkyl phenyl sulfoxide or an alkyl heteroaryl sulfoxide as the dimethylsulfoxide adduct requires longer heating to effect complete elimination and very little of the tert. allylic alcohol is produced as a result of dehydration.

The time for reaction of the sulfoxide anion with the spiro-2'-oxirane is about 120–240 min. at rt to 60° C. The mixture is then treated with water and the product is isolated by conventional work-up (precipitation from water and/or extraction with an organic solvent and evaporation of the solvent) to afford the γ-hydroxysulfoxide.

Scheme 1

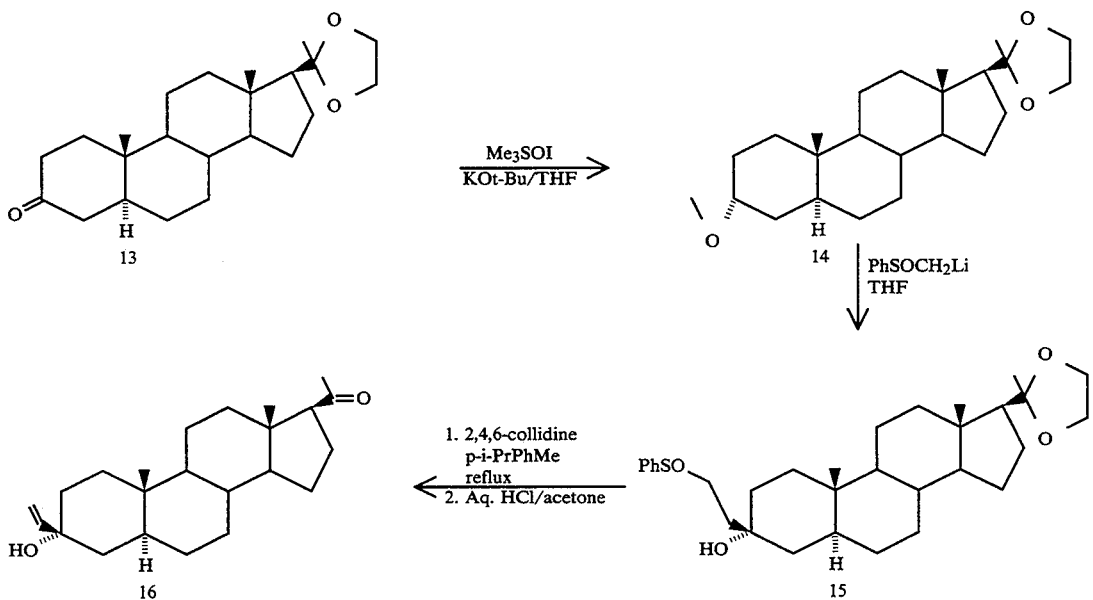

With respect to the preparation of 3β-ethenyl-3α-hydroxy-5α-pregnan-20-one according to the process of the present invention, the epoxide opening and sulfoxide elimination process is clearly an improvement as it selectively gives the 3β-ethenyl-3α-hydroxy isomer (the old method involving the addition of a vinyl magnesium halide or vinyl lithium to the 3-ketone gives a ca. 1:1 ratio of isomers. See, U.S. Pat. No. 5,232,917).

Examples of inert solvents which can be used in the practice of steps (a) and (b) of the invention include, but are not limited to, ether solvents such as tetrahydrofuran (THF), diethyl ether, 1,2-dimethoxyethane, 2-methoxyethyl ether, dimethylsulfoxide and the like. Of course, the solvent should be dried before use, for example, over molecular sieves or by distillation from lithium aluminum hydride, sodium benzophenone or calcium hydride.

The steroidal γ-hydroxysulfoxide obtained is then subjected to thermolysis at 120° to 180° C. in an inert solvent containing a base other than calcium carbonate for 45 min. to 12 h to give the steroidal allylic tertiary alcohol. Examples of inert solvents which can be used in the thermolysis of step (c) include, but are not limited to chlorobenzene, dichlorobenzenes, alkyl and dialkylbenzenes including toluene, xylenes, cumene and p-isopropyltoluene.

Bases that may be used in step (c) of the process of the invention include pyridines and related bases, i.e. pyridine, lutidine, 2-6-di-tert-butyl-4-methylpyridine, quinoline, 2-methylquinoline (quinaldine), and 2,6-dimethylquinoline; imidazole; simple alkylamines such as triethylamine, dicyclohexylamine, diisopropylamine, and diisopropylethylamine, as well as 1,4-diazabicyclo[2.2.2]octane (DABCO). Non-amine bases which may be used include sodium bicarbonate and disodium phosphate. Generally, the conjugate acid of the base may have a pKa of about 5 to 10. However, $CaCO_3$ must be avoided as this base causes excessive dehydration in the methyl or methyl phenyl sulfoxide adduct thermolysis reaction, although significantly more dehydration is observed when the dimethylsulfoxide adduct is thermolyzed. Thus, preferred adducts are prepared from methyl aryl sulfoxides or methyl heteroaryl sulfoxides.

The following examples are merely illustrative and not limitative of the remainder of the disclosure.

EXAMPLES

Example 1

Preparation of 20,20-ethylenedioxy-3α-hydroxy-3β-[2-(phenylsulfinyl)ethyl]-5α-pregnane.

A solution of diisopropylamine (freshly distilled from $CaH_2$; 0.93 mL, 673 mg, 6.68 mmol) in 4 mL of dry THF was cooled to −15° C. and treated with a 1.6M solution of n-BuLi in hexanes (Aldrich; 2.5 mL, 4.0 mmol) added dropwise via syringe. The reaction mixture was cooled to −75° C. and a solution of freshly distilled methyl phenyl sulfoxide (Aldrich; 585 mg, 4.18 mmol) in 2.5 mL of THF was added dropwise via syringe. After stirring at −75° C. for 15 min., (3-R)-20,20-ethylenedioxy-5α-pregnane-spiro-2′-oxirane (750 mg, 2.0 mmol, U.S. Pat. No. 5,232,917) was added in one portion as a solid. The reaction was then allowed to warm to rt and stirred overnight. TLC showed complete consumption of the epoxide. The reaction was cooled to 0° C. and added to an ether/water mixture in a separatory funnel. The aqueous layer was separated and extracted twice with ether. The pooled ether layers were back extracted with a saturated NaCl solution, dried ($Na_2SO_4$) and concentrated. The residue was triturated with 50 mL of water. The white solid which formed was isolated and found to be contaminated with methyl phenyl sulfoxide. After stirring vigorously in 10 mL of water overnight, the remaining methyl phenyl sulfoxide was removed, giving 966 mg (94%) of the title compound as a white solid. $^1$H NMR ($CDCl_3$, 300 MHz) δ7.63-7.50 (m, 5H), 4.02-3.73 (m, 4H), 3.07 (m, 1H), 2.86 (m, 1H), 2.00 (d, 1H), 1.90-0.80 (m, 25H), 1.28 (s, 3H), 0.74 (s, 3H), 0.71 (s, 3H).

Example 2

Preparation of 3β-ethenyl-3α-hydroxy-5α-pregnan-20-one.

A solution of the sulfoxide obtained in Example 1 (966 mg, 1.88 mmol) in 14 mL of dry p-isopropyltoluene containing 0.93 mL (857 mg, 7.1 mmol) of freshly distilled 2,4,6-collidine was heated at reflux (172° C., oil bath temperature 185° C.) for 45 min. Once the reaction had cooled to room temperature, the solvent was removed in vacuo (0.05 mmHg, 30° C.). The residue was dissolved in a minimum volume of $CH_2Cl_2$ and added to 26 cm of flash silica in a 1 cm diameter column. Elution with 100% $CH_2Cl_2$ gave crude 20,20-ethylenedioxy-3β-ethenyl-3α-hydroxy-5α-pregnane as a light yellow solid. This material was dissolved as much as possible in 45 mL of acetone and treated with an aqueous 1M HCl solution (1.2 mL). After 30 min., the solution was treated with 2 mL of a saturated $NaHCO_3$ solution and concentrated in vacuo. The residue was triturated with water and filtered to give 503 mg of a yellow solid. Recrystallization from hexane/acetone (1:1) gave 174 mg of the desired alkene, mp 161.5°–164° C. The mother liquor was concentrated to dryness and the residue was recrystallized from methanol and from hexane to give an additional 140 mg of alkene, mp 162°–164.5° C. The total yield of 3β-ethenyl-3α-hydroxy-5α-pregnan-20-one from (3-R)-20,20-ethylenedioxy-5α-pregnane-spiro-2′-oxirane was 48%. $^1$H NMR ($CDCl_3$, 300 MHz) δ5.92 (dd, 1H, J=17.3, 10.7 Hz), 5.22 (d, 1H, J=17.3 Hz), 5.00 (d, 1H, J=10.7 Hz), 2.53 (t, 1H, J=8.9 Hz), 2.20-1.98 (m, 2H), 2.11 (s, 3H), 1.70-0.80 (m, 20H), 0.78 (s, 3H), 0.60 (s, 3H).

Example 3

Elimination of 20,20-Ethylenedioxy-3α-hydroxy-3β-[2-(phenylsulfinyl)ethyl]-5α-pregnane in the Presence of $CaCO_3$.

A solution of 20,20-ethylenedioxy-3α-hydroxy-3β-[2-(phenylsulfinyl)ethyl]-5α-pregnane (15 mg, 0.029 mmol) in 0.5 mL of p-isopropyltoluene was treated with solid $CaCO_3$ (13 mg, 0.13 mmol). The resulting mixture was heated at reflux for 45 min. Concentration of the reaction mixture in vacuo gave a yellow semisolid. By $^1$H NMR (300 MHz, $CDCl_3$) and TLC (15% acetone/hexane, UV detection), extensive dehydration and deketalization to 3-ethenylpregn-3-en-20-one and/or 3-ethenylpregn-2-en-20-one had taken place. The ratio of the dehydration products to the desired allylic alcohols (20-ketal and 20-ketone) was 1:1 by $^1$H NMR.

Example 4

Elimination of 20,20-Ethylenedioxy-3α-hydroxy-3β-[2-(methylsulfinyl)ethyl]-5α-pregnane in the Presence of $CaCO_3$.

A mixture of 20,20-ethylenedioxy-3α-hydroxy-3β-[2-(methylsulfinyl)ethyl]-5α-pregnane (55 mg, 0.121 mmol) and $CaCO_3$ (36 mg, 0.36 mmol) in 1 mL of p-isopropyltoluene was heated at reflux for 105 min. By TLC (25% acetone/hexane, UV detection), little of the desired allylic alcohol was present. The presence of non-polar UV active compounds indicated that dehydration of the 3α-hydroxy group had occurred.

Example 5

Synthesis of 3α-Hydroxy-3β-[2-(E)-phenylethenyl]-5α-pregnan-20-one

Benzyl phenyl sulfoxide. To a solution of benzyl phenyl sulfide (Aldrich; 1.068 g, 5.33 mmol) in 25 mL of CH$_2$Cl$_2$ at −78° C. was slowly added a solution of m-chloroperbenzoic acid (Aldrich, 50–60%; 760 mg, 2.64 mmol if 60%) in 10 mL of CH$_2$Cl$_2$. After warming to room temperature and stirring overnight, the solution was added to 20 mL of a saturated NaHCO$_3$ solution. The aqueous layer was separated and extracted with CH$_2$Cl$_2$ (2×10 mL). The pooled organic layers were then dried (MgSO$_4$) and concentrated. The residue was subjected to flash column chromatography (silica gel, 10% acetone/hexane and 15% acetone/hexane) affording the sulfoxide (632 mg, 55%) as a white solid, mp 123°–126° C. $^1$H NMR (CDCl$_3$, 300 MHz) δ7.40-7.15 (m, 8H), 6.91 (d, 2H, J=7.8 Hz), 4.03 (d, 1H, J=12.6 Hz), 3.93 (d, 1H, J=12.6 Hz).

20,20-Ethylenedioxy-3α-hydroxy-3β-[[2-(phenylsulfinyl)-2-phenyl]ethyl]-5α-pregnane. A solution of diisopropylamine (Aldrich, freshly distilled from CaH$_2$; 0.5 mL, 361 mg, 3.57 mmol) in 2 mL of dry THF was cooled to −10° C. and treated with a 1.6M solution of n-BuLi in hexanes (Aldrich; 1.09 mL, 1.6 mmol) added dropwise via syringe. After 10 min., the reaction was cooled to −75° C. and a solution of benzyl phenyl sulfoxide (347 mg, 1.60 mmol) in 5 mL of dry THF was added dropwise via syringe over 30 min. To the resulting deep yellow solution was added 297 mg (0.79 mmol) of solid 20,20-ethylenedioxy-3(R)-5α-pregnan-3-spiro-2′-oxirane. The reaction was allowed to warm to rt and added to 30 mL of ice-cold water. The resulting mixture was extracted with EtOAc (3×20 mL). The combined EtOAc layers were back extracted with a sat. NaCl solution, dried (Na$_2$SO$_4$) and concentrated. The residue was purified by flash chromatography (silica gel, gradient from 100% CH$_2$Cl$_2$ to 20% acetone/CH$_2$Cl$_2$) affording the sulfoxide (405 mg, 86%) as a mixture of two diastereomers. This mixture was carried on to the elimination step.

3α-Hydroxy-3β-[2-(E)-phenylethenyl]-5α-pregnane-20-one. A suspension of the sulfoxide (200 mg, 0.339 mmol) in 1.5 mL of p-isopropyltoluene containing 0.2 mL of 2,4,6-collidine (distilled from CaH$_2$) was heated in an oil bath at 135° C. for 60 min. After cooling to rt, the solution was allowed to stir overnight. A white precipitate formed and was isolated and washed with p-isopropyltoluene (3×1 mL). By $^1$H NMR and TLC, the precipitate (69 mg, 44%) was the desired 20,20-ethylenedioxy-3α-hydroxy-3β-[2 -(E)-phenylethenyl]-5α-pregnane No evidence for the corresponding Z-isomer was found. A solution of the ketal in acetone at 0° C. was treated with a 1M HCl solution and stirred cold for one hour. The reaction was poured into an EtOAc/water mixture and the organic layer was washed with water and a sat. NaCl solution. After drying (Na$_2$SO$_4$), the solvent was removed in vacuo and the residue was purified by flash chromatography (silica gel, eluted with 1% acetone/CH$_2$Cl$_2$). $^1$H NMR (300 MHz CDCl$_3$) δ7.44-7.20 (m, 5H), 6.61 (d, 1H, J=16.2 Hz), 6.29 (d, 1H, J=16.2 Hz), 2.54 (t, 1H), 2.22-1.98 (m, 2H), 2.12 (s, 3H), 1.82-0.77 (m, 19H), 0.82 (s, 3H), 0.62 (s, 3H).

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A method for the preparation of a steroidal allylic tertiary alcohol, comprising (a) reaction of a sulfoxide having the formula R—S(O)CR$_1$R$_2$H, wherein R is aryl, substituted aryl, heteroaryl or substituted heteroaryl, R$_1$ is hydrogen, lower alkyl, aryl, substituted aryl or halogen; and R$_2$ is hydrogen or lower alkyl; with a strong base which is capable of deprotonating the methine hydrogen which is α to the sulfoxide, in the presence of an inert solvent, to give an anion;

(b) reaction of the anion obtained in step (a) with a steroidal spiro-2′-oxirane to give a steroidal γ-hydroxysulfoxide;

(c) thermolysis of the steroidal γ-hydroxysulfoxide obtained in step (b) in the presence of a base other than calcium carbonate to give the steroidal allylic tertiary alcohol.

2. The method of claim 1, wherein said strong base of step (a) is lithium diisopropylamide.

3. The method of claim 1, wherein said base of step (c) is 2,4,6-collidine.

4. The method of claim 1, wherein said sulfoxide is methyl phenyl sulfoxide.

5. The method of claim 1, wherein said inert solvent is THF.

6. The method of claim 1, wherein said thermolysis reaction is carried out at a temperature of 120° to 180° C.

7. The method of claim 1, wherein said steroidal allylic tertiary alcohol has the formula:

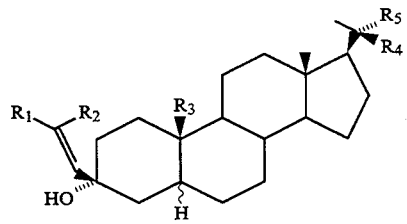

I wherein R$_1$ is hydrogen, lower alkyl, aryl, substituted aryl or halogen; R$_2$ is hydrogen or lower alkyl; R$_3$ is hydrogen or methyl; and R$_4$ and R$_5$ are independently oxo, hydrogen or hydroxy, but not both oxo or both hydrogen or both hydroxy; and wherein one or more double bonds may be present at the 1, 4, 5(6), 8(14), 9(11), 11 and 15 positions.

8. The method of claim 1, wherein said steroidal allylic tertiary alcohol has the formula:

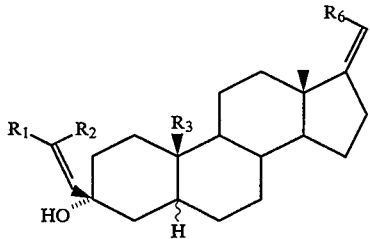

II wherein $R_1$ is hydrogen, lower alkyl, aryl, substituted aryl or halogen; $R_2$ is hydrogen or lower alkyl; $R_3$ is hydrogen or methyl; and $R_6$ is methyl or hydroxy; and wherein one or more double bonds may be present at the 1, 4, 5(6), 8(14), 9(11), 11 and 15 positions.

9. The method of claim 1, wherein said sulfoxide is methyl phenyl sulfoxide, said steroidal spiro-2'-oxirane is (3-R)-20,20-ethylenedioxy-5α-pregnane-spiro-2'-oxirane, and said steroidal allylic tertiary alcohol is 20,20-ethylenedioxy-3-ethenyl-3α-hydroxy-5α-pregnane.

10. The method of claim 1, wherein said sulfoxide is benzyl phenyl sulfoxide, said steroidal spiro-2'-oxirane is 20,20-ethylenedioxy-3(R)-5α-pregnane-3-spiro-2'-oxirane, and said steroidal allylic tertiary alcohol is 20,20-ethylenedioxy-3α-hydroxy-3β-[2-phenylethenyl]-5α-pregnane.

* * * * *